United States Patent [19]

Labianca

[11] Patent Number: 4,769,016

[45] Date of Patent: Sep. 6, 1988

[54] VENOUS CATHETER

[76] Inventor: Michele Labianca, Via Gorizia 182, Torino, Italy

[21] Appl. No.: 15,467

[22] Filed: Feb. 17, 1987

[30] Foreign Application Priority Data

Oct. 28, 1986 [IT] Italy .............................. 67812 A/86

[51] Int. Cl.$^4$ ............................................ A61M 25/00
[52] U.S. Cl. .................................... 604/280; 604/270; 604/266
[58] Field of Search ...................... 128/343, 325, 348.1, 128/658; 604/4.43, 93, 264, 270, 266, 280–284

[56] References Cited

U.S. PATENT DOCUMENTS

| | | | |
|---|---|---|---|
| 3,783,454 | 1/1974 | Sausse et al. .................. | 604/280 X |
| 3,890,976 | 6/1975 | Bazell et al. .................... | 604/280 X |
| 4,282,875 | 8/1981 | Serbinenko et al. ............. | 128/325 |
| 4,375,816 | 3/1983 | Labianca ........................ | 604/8 |
| 4,680,029 | 7/1987 | Ranford et al. ................. | 604/280 |

Primary Examiner—Dalton L. Truluck
Attorney, Agent, or Firm—Sughrue, Mion, Zinn, Macpeak, and Seas

[57] ABSTRACT

A venous catheter comprising a flexible and resilient tube of synthetic polymer, provided with a tubular tip made of titanium alloy, which confers to the end of the catheter both inherent antithrombogenic properties and a mass such as to substantially prevent the excitation of oscillations of the catheter caused by the pulsations of the venous flow and the cardiac muscle contractions. The catheter is suitable for intravenous extended perfusions and for use in peritoneo-venous shunting systems in the treatment of ascites.

16 Claims, 2 Drawing Sheets

VENOUS CATHETER

BACKGROUND OF THE INVENTION

The present invention relates to a venous catheter, comprising a flexible and resilient tube of synthetic polymer, such as silicone rubber, a terminal section of which is adapted to be inserted into the superior or inferior vena cava, in such a manner to place a free end of the terminal section at, or close to the cavo-atrial junction in order to introduce a liquid into the blood cycle.

Venous catheters of silicone rubber or other synthetic polymers are used to carry out intravenous extended perfusions, for instance for parenteral feeding purposes. These catheters are inserted into the venous systems for the treatment of ascites. In these systems a perforated tubular flexible probe, made of synthetic polymer, which is to be placed in the peritoneal cavity to drain the ascitic fluid, is connected to the catheter through a check valve. The end part of the catheter is to be inserted in the superior vena cava where the ascitic liquid will be discharged.

These shunting systems are known, for instance, from U.S. Pat. No. 3,910,283 and their application is becoming more and more widespread. Their implantation and other features are described in various publications, such as Le Veen, H. H., Christoudias, G., Ip, M., Luft, R., Falk, G., Crosbery, S., "Peritoneo-venous shunting for ascites", Ann. Surg., 180, 1974, 580–591 and Le Veen, H. H., Wapnick S., "Operative details of continuous peritoneo-venous shunt for ascites", Bulletin de la Société Internationale de Chirurgie, 6, 1974, 579–582.

In these known systems the whole catheter is made of silicone rubber, although the use of other biologically inert, synthetic polymers is not excluded. They have frequently caused the severe disadvantage of short-term occlusion of the catheter due to the formation of deposits or thrombi. This disadvantage is linked to various factors connected to the presence of calcium ions in the blood, to the properties of the ascitic fluid and the mechanic and biochemical characteristics of the catheter of polymer.

Particularly in the case of cirrhotic ascites the ascitic liquid is rich of procoagulant factors which encourage the formation of thrombi. It has however been established that, as the ascitic liquid is drained, the formation of occlusions due to thrombi does not decrease. Probably this is due to the fact that the outlet opening of the catheter has a rather sharp edge, and the catheter, comprising a flexible and elastic tube, oscillates in the vein in synchronism with the blood pulsations and the heart beat, thus causing lesions to the wall of the vein, with the consequent formation (which has been proven) of parietal thrombi.

The same severe disadvantages occur with catheters used for intravenous perfusions. These catheters, especially in the case of parenteral feeding, are subject to occlusions within two or three days from the implantation, whereas they would be required to function for periods of one or more months.

The object of the present invention is to provide a venous catheter with a negligible risk of occlusions compared to the known catheters.

SUMMARY OF THE INVENTION

According to the present invention, the aforesaid object is achieved by means of a venous catheter wherein the terminal section of the flexible tube of synthetic polymer is provided, at said free end, with a tubular tip made of a titanium alloy, said tip having an inner axial through-bore or duct, whereby said tip is adapted to give to said free end both inherent antithrombogenic properties and a mass such as to substantially prevent the excitation of oscillations of the catheter caused by the pulsations of the blood flow and the rhythmical movements of the cardiac muscle.

THEORY OF THE INVENTION

In a catheter according to the invention on one hand one takes advantage of the antithrombogenic properties of titanium, largely described in U.S. Pat. No. 4,375,816 to the same Applicant. On the other hand, the relatively heavy mass formed by the tip of titanium alloy gives to the catheter such a high mass as to make it practically insensitive to te blood pulsations and the movements of the cardiac muscle. Thus, the terminal section of the catheter can hardly move inside the vena cava or inside the cavo-atrial junction, with lower risk of parietal lesions.

Preferably, the tubular tip has, in an apex portion thereof which is designed to be exposed to the blood flow, a wall having a thickness which smoothly decreases up to a rounded, annular, relatively thin edge which defines an outlet opening of the inner bore of the tip, to encourage mutual convergence of the flow lines of the blood and of the liquid introduced into the blood though the catheter, with a laminar flow downstream of the outlet opening, whereby the liquid will be entrained by the blood thanks to an intensified interaction of their boundary layers.

On one hand this phenomenon makes the catheter more effective, as the dragging of liquid by the blood combines with the thrust due to the liquid pressure from an external vessel or from the peritoneal cavity. On the other hand the annular edge, being of rounded shape, is practically unable to damage the venous wall.

BRIEF DESCRIPTION OF THE DRAWINGS

The invention will be better understood by a reading of the following detailed description, reference being made to the attached drawings, given by way of non-limiting example, in which:

FIG. 4 is an elevational view of the tip of the catheter, and FIG. 5 is a longitudinal section of the same tip, joined to the flexible tube of the catheter.

DETAILED DESCRIPTION OF THE ILLUSTRATED EMBODIMENT

Figure 1:
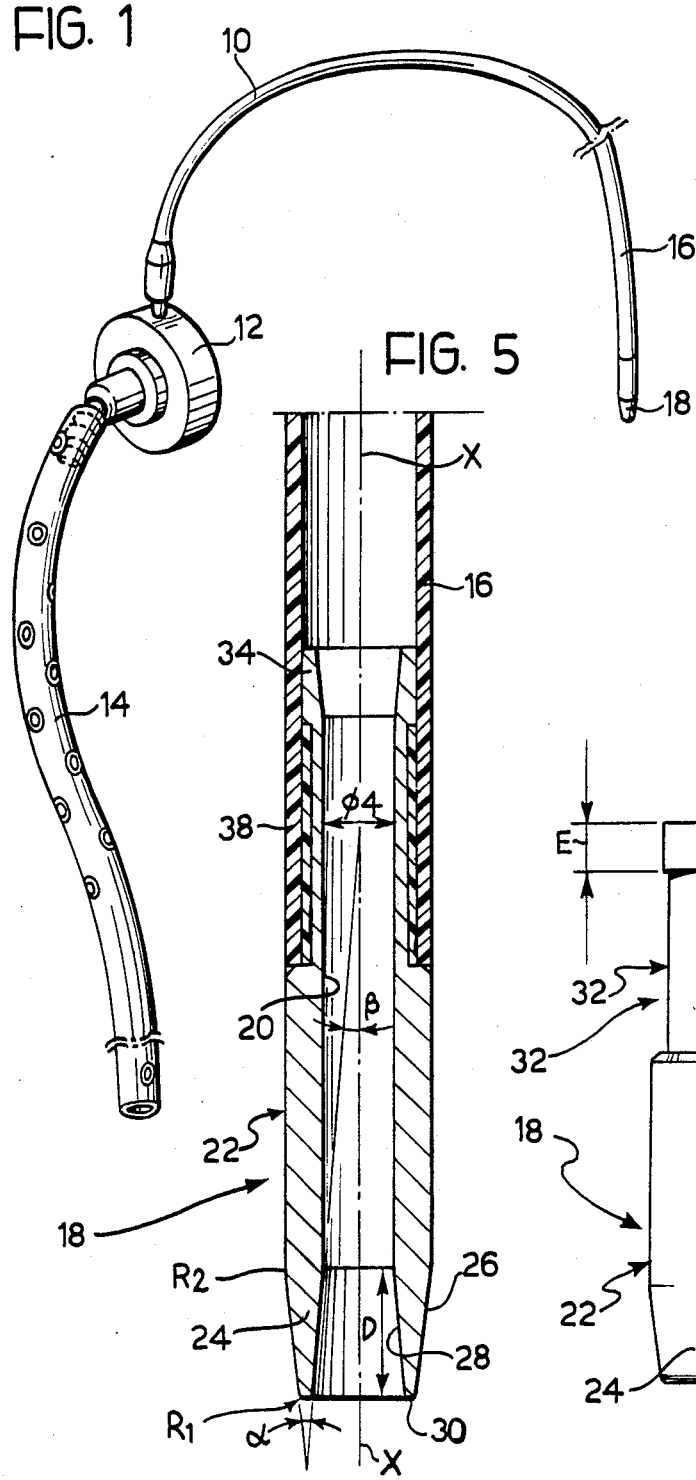
FIG. 1 is a perspective view of a peritoneo-venous shunting system provided with a catheter according to the invention.
Figure 2:
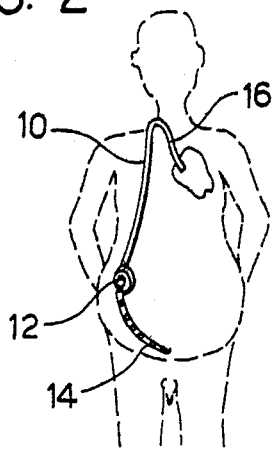
FIG. 2 is a sketch showing a subject suffering from ascites, with the shunting system fitted.

Referring to FIGS. 1 and 2, a peritoneo-venous shunting system comprises a tube 10 of flexible and resilient synthetic polymer, such as silicone rubber. The tube 10 is connected through a check valve 12 to a perforated tubular probe 14. Also the probe 14 comprises a tube of silicone rubber or other flexible synthetic polymer. A terminal section, indicated by 16, of the tube 10 is provided at its free end with a tubular tip 18, which will be described later.

The system of FIG. 1 is adapted to be implanted, as in FIG. 2, according to the technique disclosed in the literature cited in the introducing part of the present specification. More particularly, the probe 14 is placed in the peritoneal cavity through an incision made medially in respect of the front axillary line. The valve 12, which is preferably the well known Le Veen valve disclosed in U.S. Pat. No. 3,910,283, is placed in subcutaneous position through the said incision.

The tube 10 is passed, following a subcutaneous path, from the incision where the valve 12 is placed, to an incision made in the patient's neck at the level of the right inner jugular vein. Through the latter incision the jugular vein undergoes longitudinal venotomy and the terminal section 16 with its tip 18 is inserted as a catheter into the jugular vein.

Figure 3:
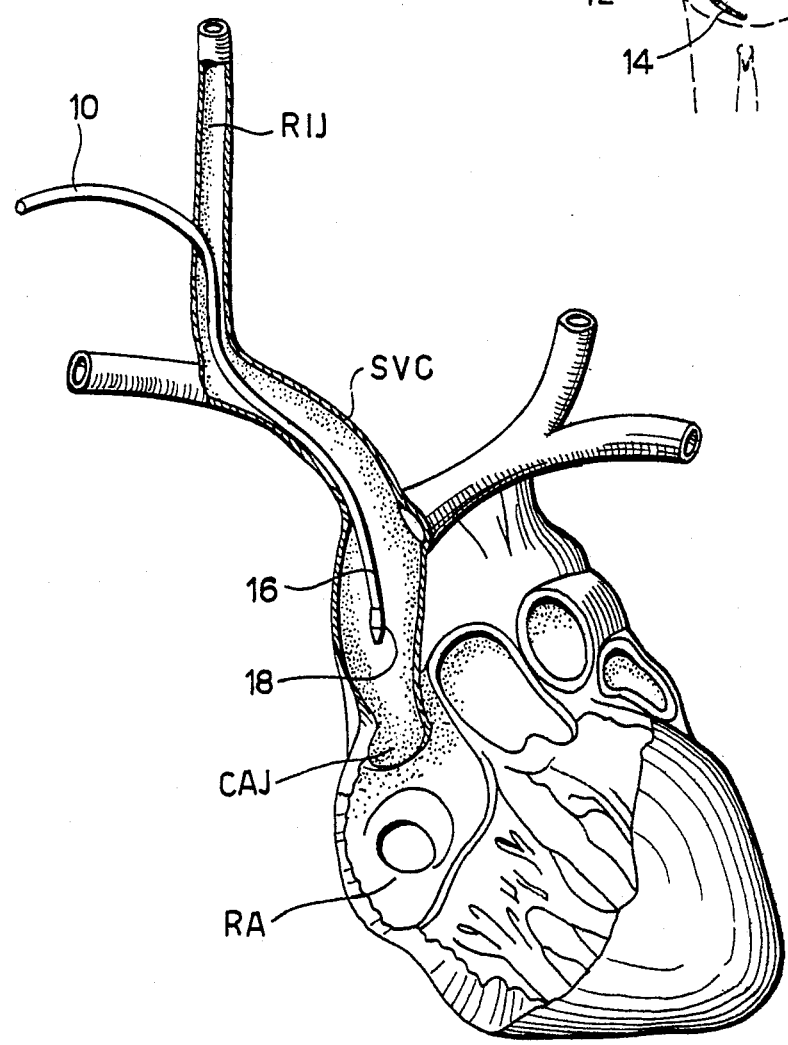
FIG. 3 is a pictorial section of the cardiac muscle, the superior vena cava and the right inner jugular vein, fitted with the catheter of the shunting system of FIG. 1.

As one can see in FIG. 3, the venous catheter 16 in the right inner jugular vein RJV is made to descend into the superior vena cava SVC, as far as the point in which the tip 18 reaches the cavo-atrial junction CAJ, where the superior vena cava opens to the right atrium RA of the heart.

The operation of the shunting system is explained in detail in the cited literature: through breathing, the intrathoracic pressure decreases with the lowering of the diaphragm and the intraperitoneal pressure increases with respect to the pressure in the superior vena cava, whereby the pressure differential impels the ascitic fluid from the peritonaeum to the vein through the valve 12, which prevents its reflux. Thus the ascitic liquid is introduced into the blood cycle.

The tip 18 shown in detail in FIGS. 4 and 5 will now be described.

This tip is made of a titanium alloy, whose composition is that of technically pure titanium.

The chosen composition is an alloy having the following specifications:

| Fe | 0.30% max | breaking load R = 53–69 kg/mm$^2$ |
| C | 0.10% max | yield point $R_S \geq$ 35 kg/mm$^2$ |
| N | 0.06% max | extensibility A% $\geq$ 16 |
| O | 0.25% max | hardness HB = 200 (approx) |
| H | 0.0125% max | |
| Ti | remainder | |

The antithrombogenic properties of titanium are already described in U.S. Pat. No. 4,375,816. Besides, titanium has an excellent chemical resistance to aggressive agents, both liquid and gaseous. Additionally, titanium can be detected by X rays, which makes it ideal for use in a catheter of a shunting system.

Referring now to FIGS. 4 and 5, the tip 18 is tubular, i.e. it has an inner axial duct or through-bore 20 which is mainly cylindrical. The axis of the tip and its inner bore 20 is indicated by X.

The tip 18 comprises a main section 22 with a larger diameter, which, for the most part of its length, an outer cylindrical shape. The main section 22 ends with an apex portion 24 whose wall has a thickness which smoothly decreases towards its end. More particularly, and preferably, in the apex portion 24 the external surface 26 converges towards the axis X by a small angle $\alpha$, whereas the surface 28 of the inner duct diverges from the axis X by a small angle $\beta$. The two surfaces 26 and 28 join together at an annular edge 30, with a rounded, relatively thin profile, which defines the outlet opening of the inner duct 20. The surface 26 gently merges to the external cylindrical surface of the main section 22.

The tip 18 further comprises a coupling section or spigot 32, which has a diameter smaller than that of the main section 22. At the opposite end of the apex portion 24, the spigot 32 ends with a collar 34 having a slightly larger diameter.

The spigot 32 is adapted to be inserted into the end of the flexible tube catheter 16, as shown in FIG. 5. As can be seen, a long annular groove 36 is defined around the spigot 32 between the main section 22 and the collar 34. The groove 36 receives a layer of adhesive 38 which keeps the tip 18 and the catheter 16 firmly joined. One can see that the diameters of the main section 22 and of the spigot 32 are such that the outer surface of the end of the tubular section 16, when fitted around the spigot 32, is flush with the outer surface of the main section 22.

The union of the catheter 16 with its tip 18 through the adhesive 38 is advantageous, as it allows the joining of the tip to the catheter to be carried out while the patient is operated on, utilising on one hand a traditional shunting system, without tip, taken from a sterile pack, and on the other hand a tip, taken as well from a sterile pack.

The sterilised adhesive which is used is preferably a silicone bonding-sealing agent like the one produced by Medtronic, Inc., marketed under the trademark "MEDTRONIC" and indicated by part No. 080118. This adhesive agent has the advantage of hardening in a few seconds.

The preferred dimensional characteristics of the tip 18 which is to be used with a tube of silicone (10, 16) having an external diameter of 5.7 mm and an internal diameter of 3.5 mm will now be indicated.

The dimensions of the tip are indicated by reference letters in FIGS. 4 and 5.

| A = 29 mm | $\phi_1$ = 5.7 mm |
| B = 17 mm | $\phi_2$ = 3.5 mm |
| C = 12 mm | $\phi_3$ = 3.5 mm |
| D = 5 mm | $\phi_4$ = 3 mm |
| E = 2.5 mm | $R_1$ = 0.5 mm |
| $\alpha = \beta = 5°$ | $R_2$ = 10 mm |

With these dimensions one obtains a tip of 1.26 grams in weight. This tip replaces a section of flexible tube of silicone rubber of a length B of 17 mm, which would have a weigth as low as 0.45 grams.

It has been found that a tip 18 of the aforesaid weight of 1.26 grams, when fitted as in FIG. 3 at the end of the catheter 16 which is, for example, suspended in the superior vena cava constitutes, a mass which renders the catheter 16 practically insensitive to the pulsations of the blood flow and to the rhythmical movements of the cardiac muscle. In the absence of the tip 18, the flexible catheter is instead easily excited by the pulsations of the blood flow and by the rhythmical movements of the heart, and begins to oscillate instead of remaining in a substantially steady position. It is these movements of the catheters according to the prior art that caused parietal lesions with subsequent thrombi.

Another advantage of the tip 18 according to the invention is due to the progressively decreasing thickness of its apex portion 24 exposed to the blood flow, and to the rounded shape of the annular edge 30. Already the rounded edge 30 in itself is not capable to damage the vein wall when the catheter is being fitted and when it is in situ. Moreover, the tapering of the wall to the rounded edge 30, which is relatively thin, encourages the mutual convergence, with a laminar flow, of the flow lines of the blood and of the ascitic fluid, downstream of the outlet opening. Thus, the ascitic liquid is entrained by the blood thanks to an intensified interaction of their boundary layers. Besides, the configuration shown of the apex portion 24, which does not cause sudden deviations in the flows, prevents even more the formation of vortexes which, in turn, could cause thrombi.

So far, twenty patients suffering from peritoneal ascites have been treated with a shunting system fitted with a tip, according to the invention, with the preferred features just described. The system has been implanted for over six months in eighteen of these patients, and no occulsions have occurred.

There have been no postoperative complications in any of these patients. One of the patients died one month later, and another patient four months after the operation, both suffering from complications unrelated to the operation itself and to the fitted shunting system. There has been no intolerance reported by any patient towards the materials used for the shunting system.

These results are encouraging if compared with the high percentage of occlusions reported in patients treated with peritoneo-venous shunting systems according to the prior art (about 20% of occulsions in patients treated from 1976 to 1983).

Although the description referring to the drawings has been given for a venous catheter which is part of a shunting system, it is understood that a catheter comprising a flexible tube as 10 and a tip as 18 can be used with the same advantage for intravenous perfusions carried out in the superior vena cava or in the inferior vena cava.

I claim:
1. A venous catheter comprising a flexible and resilient tube of synthetic polymer, such as silicon rubber, one terminal section of which is adapted to be inserted into the superior or inferior vena cava in such a manner to place a free end of said terminal section at, or close to, the cavo-atrial junction in order to introduce a liquid into the blood cycle, wherein the end of the terminal section of the flexible tube of synthetic polymer is provided, at said free end, with a tubular tip made of a titanium alloy, said tip having a length greater than the diameter and having an inner axial through-bore or duct, whereby said tip is adapted to give to said free end both inherent anti-thrombogenic properties and a mass such as to substantially prevent the excitation of oscillations of the catheter caused by the pulsations of the blood flow and the rhythmical movements of the cardiac muscle and
    wherein the tubular tip has, in an apex portion thereof which is adapted to be exposed to the blood flow, a wall having a thickness which smoothly decreases up to a rounded annular, relatively thin edge which defines an outlet opening of the inner bore of the tip to encourage mutual convergence of the flow lines of the blood and of the liquid introduced into the blood through the catheter, with a laminar flow downstream of the outlet opening, whereby the liquid will be entrained by the blood due to an intensified interaction of their boundary layers.

2. A venous catheter as claimed in claim 1, wherein said apex portion of the tip has an outer surface which converges towards the axis of the tip.

3. A venous catheter as claimed in claim 2, wherein said outer surface has an angle of convergence with respect to said axis of the order of 5°.

4. A venous catheter as claimed in claim 3, wherein in the apex portion of the tip said inner bore has a surface diverging from said axis.

5. A venous catheter as claimed in claim 4, wherein said diverging surface of the inner bore makes an angle of the order of 5° with said axis.

6. A venous catheter as claimed in claim 1, wherein said annular edge which defines the outlet opening of the inner bore is rounded with a radius of the order of 0.5 mm.

7. A venous catheter as claimed in claim 1, wherein the tip comprises a main section designed to be exposed to the blood flow and a coupling section or spigot having an outer diameter smaller than that of the main section and around which the corresponding end of said terminal section of the flexible tube is fitted, the diamter of the coupling section being such that the outer surface of said end of the terminal section is flush with the external surface of the main section of the tip.

8. A venous catheter as claimed in claim 7, wherein the coupling section at the tip has, at an end thereof which is away from said main section, a collar of enlarged diameter, so as to define between the main section and the collar an outer annular groove, such groove being filled with biocompatible adhesive fixing the terminal section to the coupling section.

9. A tip adapted to be connected to a free end of a venous catheter comprising a flexible tube of relatively resilient synthetic polymer, such as silicone rubber, said tip comprising a tubular element made of titanium alloy, having a length greater than the diameter and having an inner axial through-bore or duct, whereby said tip is adapted to give to said free end of the catheter both inherent anti-thrombogenic properties and a mass such as to substantially prevent the excitation of oscillations of the catheter caused by the pulsations of the blood flow and by the rhythmical movements of the cardiac muscle and
    wherein the tip has, in an apex portion thereof which is adapted to be exposed to the blood flow, a wall having a thickness which smoothly decreases up to a rounded annular relatively thin edge defining an outlet opening of the inner bore of the tip to encourage mutual convergence of the flow lines of the blood and the liquid introduced into the blood through the catheter with a laminar flow downstream of the outlet opening, whereby the liquid will be entrained by the blood due to an intensified interaction of their boundary layers.

10. A tip as claimed in claim 9, wherein said apex portion has an outer surface which converges towards the axis of the tip.

11. A tip as claimed in claim 10, wherein said outer surface has an angle of convergence with respect to said axis of the order of 5°.

12. A tip as claimed in claim 11, wherein in the apex portion of the tip said inner bore has a surface diverging from said axis.

13. A tip as claimed in claim 12, wherein said diverging surface of the inner bore makes an angle of the order of 5° with said axis.

14. A tip as claimed in claim 9, wherein said annular edge which defines the outlet opening of the inner bore is rounded with radius of the order of 0.5 mm.

15. A tip as claimed in claim 9, wherein the tip comprises a main section designed to be exposed to the blood flow and a coupling section or spigot having an outer diameter smaller than that of the main section and around which the corresponding end of the flexible tube catheter is designed to be fitted, the diameter of the coupling section being such that the outer surface of said end of the catheter will be flush with the outer surface of the main section.

16. A tip as claimed in claim 15, wherein the coupling section of the tip has, at an end thereof which is away from said main section, a collar of enlarged diameter, so as to define between the main section and the collar an external annular groove which is adapted to be filled with a biocompatible adhesive to fix the catheter to the coupling section.

* * * * *